(12) United States Patent
Korenev

(10) Patent No.: US 8,875,560 B2
(45) Date of Patent: Nov. 4, 2014

(54) SYSTEM IMPLEMENTING CONSTITUENT IDENTIFICATION AND CONCENTRATION DETECTION

(75) Inventor: Sergey Korenev, Mundelein, IL (US)

(73) Assignee: Caterpillar Inc., Peoria, IL (US)

( * ) Notice: Subject to any disclaimer, the term of this patent is extended or adjusted under 35 U.S.C. 154(b) by 631 days.

(21) Appl. No.: 13/174,418

(22) Filed: Jun. 30, 2011

(65) Prior Publication Data

US 2013/0000386 A1    Jan. 3, 2013

(51) Int. Cl.
| | | |
|---|---|---|
| *G01N 9/00* | (2006.01) | |
| *G01N 7/00* | (2006.01) | |
| *F01N 11/00* | (2006.01) | |
| *G01M 15/00* | (2006.01) | |
| *G01N 27/407* | (2006.01) | |

(52) U.S. Cl.
CPC *F01N 11/00* (2013.01); *G01N 9/00* (2013.01); *G01N 7/00* (2013.01); *G01N 27/4077* (2013.01); *F01N 2560/02* (2013.01); *G01M 15/00* (2013.01); *Y02T 10/47* (2013.01)
USPC ........................................................ 73/31.05

(58) Field of Classification Search
CPC . G01N 27/4077; G01N 27/21; G01N 27/414; G01N 27/3504
USPC ........................................................ 73/31.05
See application file for complete search history.

(56) References Cited

U.S. PATENT DOCUMENTS

| | | |
|---|---|---|
| 3,559,049 A | 1/1971 | Liebermann et al. |
| 3,980,530 A | 9/1976 | Hueser |
| 4,260,884 A | 4/1981 | Lovelock |
| 4,272,995 A | 6/1981 | Weistra |
| 4,531,486 A | 7/1985 | Reif et al. |
| 4,665,690 A | 5/1987 | Nomoto et al. |
| 4,705,947 A | 11/1987 | Ramsey et al. |
| RE32,552 E | 12/1987 | Liebermann et al. |

(Continued)

FOREIGN PATENT DOCUMENTS

| | | |
|---|---|---|
| DE | 10229411 A1 | 1/2004 |
| DE | 102004007647 B4 | 4/2006 |

(Continued)

OTHER PUBLICATIONS

U.S. Appl. No. 13/174,373, filed Jun. 30, 2011.

(Continued)

*Primary Examiner* — Hezron E Williams
*Assistant Examiner* — Rodney T Frank
(74) *Attorney, Agent, or Firm* — Finnegan, Henderson, Farabow, Garrett & Dunner LLP

(57) ABSTRACT

A gas monitoring system is disclosed. The gas monitoring system may have a first electrode, a second electrode spaced apart from the first electrode to receive a gas between the first and second electrodes, and a pulse generator configured to apply a voltage pulse, tuned to a particular constituent of the gas, to the first and second electrodes and create a non-thermal plasma between the first and second electrodes. The gas monitoring system may also have a detection controller in communication with the pulse generator. The detection controller may be configured to determine an actual current between the first and second electrodes during application of the voltage pulse, and to determine a concentration of the constituent based on the actual current and an expected identity of the constituent.

27 Claims, 7 Drawing Sheets

(56) References Cited

U.S. PATENT DOCUMENTS

| | | | |
|---|---|---|---|
| 4,916,384 | A | 4/1990 | Ishida |
| 5,198,773 | A | 3/1993 | Latta |
| 5,475,311 | A | 12/1995 | Cho et al. |
| 5,567,882 | A | 10/1996 | Ichimura et al. |
| 5,591,896 | A | 1/1997 | Lin |
| 6,090,268 | A | 7/2000 | Kunimatsu et al. |
| 6,266,993 | B1 | 7/2001 | Diehl et al. |
| 6,457,347 | B1 | 10/2002 | Koo et al. |
| 7,047,815 | B2 | 5/2006 | Sashinami et al. |
| 7,086,288 | B2 | 8/2006 | Lee et al. |
| 7,159,443 | B2 | 1/2007 | Wolf |
| 7,350,396 | B2 | 4/2008 | Huang et al. |
| 7,367,233 | B2 | 5/2008 | Nagasawa et al. |
| 7,416,650 | B2 | 8/2008 | Hatada et al. |
| 7,426,848 | B1 | 9/2008 | Li et al. |
| 7,445,700 | B2 | 11/2008 | Kato et al. |
| 7,529,633 | B1 | 5/2009 | Schipper et al. |
| 7,615,931 | B2 * | 11/2009 | Hooke et al. ............ 315/111.21 |
| 7,615,933 | B2 * | 11/2009 | Hooke et al. ............ 315/209 R |
| 7,832,254 | B2 | 11/2010 | Guenschel et al. |
| 7,955,494 | B2 | 6/2011 | Kawase et al. |
| 8,268,147 | B2 | 9/2012 | Ieda et al. |
| 8,402,812 | B2 | 3/2013 | Sasaki |
| 2006/0251543 | A1 | 11/2006 | Koratkar et al. |
| 2007/0261471 | A1 | 11/2007 | Kondo et al. |
| 2008/0028752 | A1 | 2/2008 | Lee |
| 2008/0140301 | A1 | 6/2008 | Ding et al. |
| 2010/0229632 | A1 | 9/2010 | Tokuda et al. |
| 2010/0229724 | A1 | 9/2010 | Tokuda et al. |
| 2011/0062973 | A1 | 3/2011 | Paterson |
| 2011/0128010 | A1 | 6/2011 | Gianchandani et al. |
| 2012/0272721 | A1 | 11/2012 | Kochupurackal et al. |
| 2013/0084474 | A1 * | 4/2013 | Mills ............................. 429/9 |

FOREIGN PATENT DOCUMENTS

| | | |
|---|---|---|
| EP | 0715158 | 6/1996 |
| GB | 905626 A | 9/1962 |
| JP | 56-147031 | 11/1981 |
| JP | 1984171826 A | 9/1984 |
| JP | 1985123761 A | 7/1985 |
| JP | 07-233719 | 9/1995 |
| JP | 1999258088 A | 9/1999 |
| JP | 2006300578 A | 11/2006 |
| JP | 4574411 B2 | 11/2010 |
| RU | 2146361 C1 | 3/2000 |
| SU | 426182 A1 | 4/1974 |
| SU | 655954 A1 | 4/1979 |
| SU | 729496 A1 | 4/1980 |
| WO | WO03034053 A2 | 4/2003 |

OTHER PUBLICATIONS

U.S. Appl. No. 13/174,450, filed Jun. 30, 2011.
U.S. Appl. No. 13/174,468, filed Jun. 30, 2011.
Guohua et al., "Carbon Nanotube Gas Sensor Based on Corona Discharge," *Chinese Journal of Analytical Chemistry*, vol. 34 issue 12, (2006) 1813-1816.
Kim, "Sensors based on Paschen's law using carbon nanotubes as electron emitters," *J. Phys. D: Appl. Phys.*,39 (2006) 3026-3029.
Wu et al., "A MEMS-based ionization gas sensor using carbon nanotubes and dielectric barrier," *Proceedings of the 3rd IEEE International Conference on Nano/Micro Engineered and Molecular Systems*, Jan. 6-9, 2008, Sanya, China 824-827.
Sim, et al., "Multi-purpose ionization gas sensing devices using carbon nanofibers on plastic substrates," *Diamond & Related Materials*, 17 (2008) 1959-1962.
Hou et al., "MEMS-based microelectrode system incorporating carbon nanotubes for ionization gas sensing," *Sensors and Actuators B*, 127 (2007) 637-648.
Modi et al., "Miniaturized gas ionization sensors using carbon nanotubes," *Nature*, 424 (2003) 171-175.
Hui et al., "A novel gas-ionization sensor based on aligned multi-walled carbon nanotubes," *Measurement Science and Technology*, 17 (2006) 2799-2805.
Liao et al., "A novel gas sensor based on field ionization from ZnO nanowires: moderate working voltage and high stability," *Nanotechnology*, 19 (2008) 175501.
Nikfarjam et al., "Fabrication of gas ionization sensor using carbon nanotube arrays grown on porous silicon substrate," *Sensors and Actuators A*, 162 (2010) 24-28.
Yong et al., "Study of improving identification accuracy of carbon nanotube film cathode gas sensor," *Sensors and Actuators A*, 125 (2005) 15-24.
Malik et al., "A review of electrical breakdown in mixtures of SF6 and other gases," *IEEE Trans. Electr Insul*, vol. EI-14 No. 1 (1979) 1-13.
Allan, "Carbon nanotube promise a simple approach to making gas sensors," *Small Times*, vol. 8, issue 3 (2008).
Diaz, "Miniaturized Gas Ionization Sensors using Nanomaterials," University of Puerto Rico, Graduate Chemistry Department, Graduate Seminar, Mar. 11, 2009.
Johannes et al., "Procedure and device for the monitoring of the particle concentration in a gas flow" Machine translation of DE102004007647B4.
Bernhard et al., "Procedure for determining the particle portion in a gas flow" Machine translation of DE10229411A1.
Hiroshi et al., "Capacitance type pressure sensor and vacuum degree evaluation method of vacuum chamber thereof" Machine translation of JP2006300578A.
Katsuyama et al., "A soot detection sensor and a soot detecting method" Machine translation of JP04574411B2.

\* cited by examiner

SYSTEM IMPLEMENTING CONSTITUENT IDENTIFICATION AND CONCENTRATION DETECTION

TECHNICAL FIELD

The present disclosure is directed to a gas monitoring system and, more particularly, to a gas monitoring system implementing constituent identification and concentration detection.

BACKGROUND

Internal combustion engines, including diesel engines, gasoline engines, gaseous fuel-powered engines, turbine engines, and other engines known in the art exhaust a complex mixture of air pollutants. These air pollutants are composed of gaseous compounds, such as the oxides of nitrogen ("$NO_x$"), the oxides of sulfur ("$SO_x$"), CO, $CO_2$, $NH_3$, and soot (particulate matter or "PM"). Due to increased awareness of the environment, exhaust emission standards have become more stringent, and the amounts of many of these pollutants emitted from an engine may be regulated depending on the type of engine, size of engine, and/or class of engine.

One method that has been implemented by engine manufacturers to comply with the regulation of engine exhaust pollutants has been to detect the different exhaust pollutants, and then treat the detected constituents through various reduction, conversion, and trapping processes. Many different types of constituent-detecting gas sensors are currently available for this use. Some common examples are semiconductor gas sensors, electrochemical gas sensors, and ionization gas sensors. Typical semiconductor gas sensors operate using a detection mechanism that functions based on a changing conductivity in the presence of a target gas. Although adequate for some situations, semiconductor gas sensors generally require high temperatures to operate (e.g., 200-400° C.), are sensitive to water vapor, become unstable as they age, and lack selectivity. Electrochemical gas sensors operate by oxidizing or reducing the target gas at an electrode, and measuring a resulting current. Electrochemical gas sensors, like semiconductor gas sensors, also require high temperatures (e.g., typically above 326° C.) in order to correctly operate. Finally, typical ionization sensors operate utilizing distinct ionization characteristics that a particular gas possesses. Ionization sensors traditionally require relatively high voltages, consume large amounts of power, and have bulky architectures.

One attempt to improve constituent detection within a gas is described in U.S. Pat. No. 7,529,633 (the '633 patent) issued to Schipper et al. on May 5, 2009. The '633 patent discloses a method of determining the chemical composition of a single- or multi-constituent gas, using a discharge hold-off mechanism. The method of the '633 patent includes creating a voltage between two electrodes, and holding the voltage until breakdown of a first gas constituent is observed. Assuming the gas contains multiple constituents, the method of the '633 patent further includes incrementally increasing the voltage over time until breakdown of a second constituent is observed. The step-changes in the voltage and current over time are then used to identify what constituents are present in the gas. Additionally, the method of the '633 patent includes identifying the concentrations of the detected constituents using a sum of an ion current and an electron current.

There are a number of limitations to the '633 patent's approach that may inhibit commercialization. First, the method of the '633 patent advocates using a constant voltage (i.e., non-pulsed voltage) to identify the gas constituents and their respective concentrations. In a constant voltage system, power consumption will generally be high. Moreover, in a constant voltage system, electrode erosion could become a problem due to the sustained discharge, particularly during a thermal discharge.

The gas monitoring system of the present disclosure addresses one or more of the problems set forth above and/or other problems of the prior art.

SUMMARY

In one aspect of the present disclosure relates to another gas monitoring system. This gas monitoring system may include a first electrode, a second electrode spaced apart from the first electrode to receive a gas between the first and second electrodes, and a pulse generator configured to apply a voltage pulse, tuned to a particular constituent in the gas, to the first and second electrodes and create a non-thermal plasma between the first and second electrodes. The gas monitoring system may also include a detection controller in communication with the pulse generator. The detection controller may be configured to determine an actual current between the first and second electrodes during application of the voltage pulse, and to determine a concentration of the constituent based on the actual current.

Another aspect of the present disclosure relates to another gas monitoring system. This gas monitoring system may include a first electrode, a second electrode spaced apart from the first electrode to receive a gas between the first and second electrodes, and a pulse generator configured to apply a series of voltage pulses, tuned to a particular constituent in the gas, to the first and second electrodes and create a non-thermal plasma between the first and second electrodes. The gas monitoring system may also include a detection controller in communication with the pulse generator. The detection controller may be configured to detect breakdown of the gas during application of one of the series of voltage pulses and, based on a known first parameter of the gas and a voltage amplitude of the one of the series of voltage pulses, and determine a second parameter of the gas.

Another aspect of the present disclosure relates to another gas monitoring system. This gas monitoring system may include a first electrode, a second electrode spaced apart from the first electrode to receive a gas between the first and second electrodes, and a pulse generator configured to apply a series of voltage pulses, tuned to a particular constituent in the gas, to the first and second electrodes and create a non-thermal plasma between the first and second electrodes. The gas monitoring system may also include a detection controller in communication with the pulse generator. The detection controller may be configured to determine a delay associated with a current between the electrodes at a start of breakdown of the gas caused by application of the voltage pulse, and to determine a temperature of the gas based on the delay.

DETAILED DESCRIPTION

Figure 1:
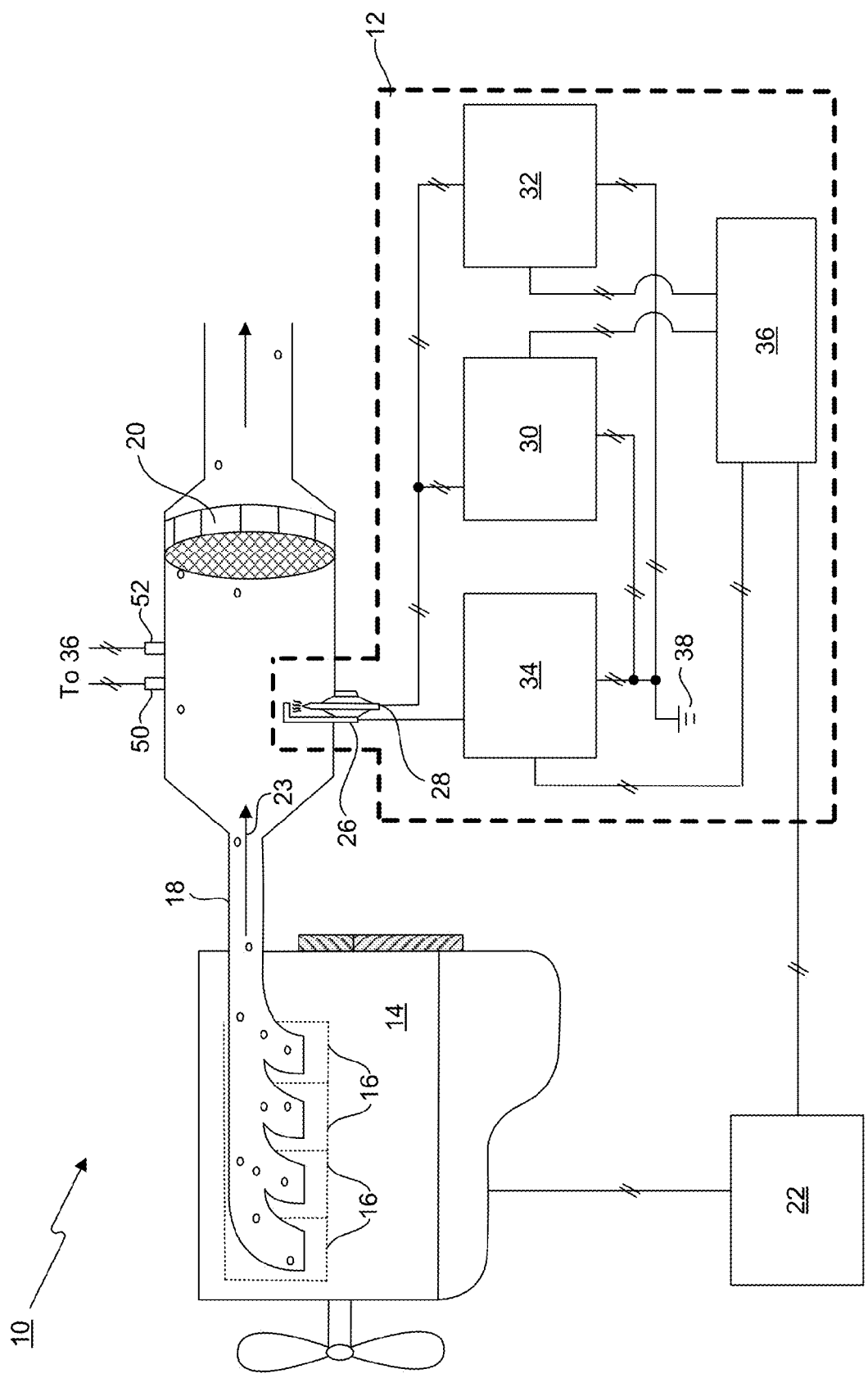
FIG. 1 is a diagrammatic illustration of an exemplary disclosed power system.

FIG. 1 illustrates an exemplary power system 10 incorporating a gas monitoring system 12 consistent with this disclosure. For the purposes of this disclosure, power system 10 is depicted and described as an internal combustion engine, for example a gasoline, diesel, or gaseous fuel-powered engine that draws in a flow of combustion gases and produces a flow of exhaust gas 23. However, it is contemplated that power system 10 may embody any other type of gas producing, treating, and/or handling system known in the art where detection of particular constituents within the associated gas is desired.

Power system 10, as an internal combustion engine, may include an engine block 14 that at least partially defines a plurality of cylinders 16, and a plurality of piston assemblies (not shown) disposed within cylinders 16. Cylinders 16, together with the pistons, may form a plurality of combustion chambers. It is contemplated that power system 10 may include any number of combustion chambers and that the combustion chambers may be disposed in an "in-line" configuration, a "V" configuration, or in any other conventional configuration. An exhaust passage 18 may extend from the combustion chambers to the atmosphere, and one or more different treatment devices 20 (e.g., particulate filters, reductant injectors, catalysts, attenuation devices, etc.) may be disposed within exhaust passage 18.

In some embodiments, power system 10 may be equipped with a general system controller 22. In these embodiments, system controller 22 may be configured to regulate operations of power system 10, for example fuel injection, boosting, gas mixing, valve timing, exhaust gas recirculation, reductant dosing, and other operations, to affect production of regulated constituents and/or their discharge to the atmosphere.

Figure 2:
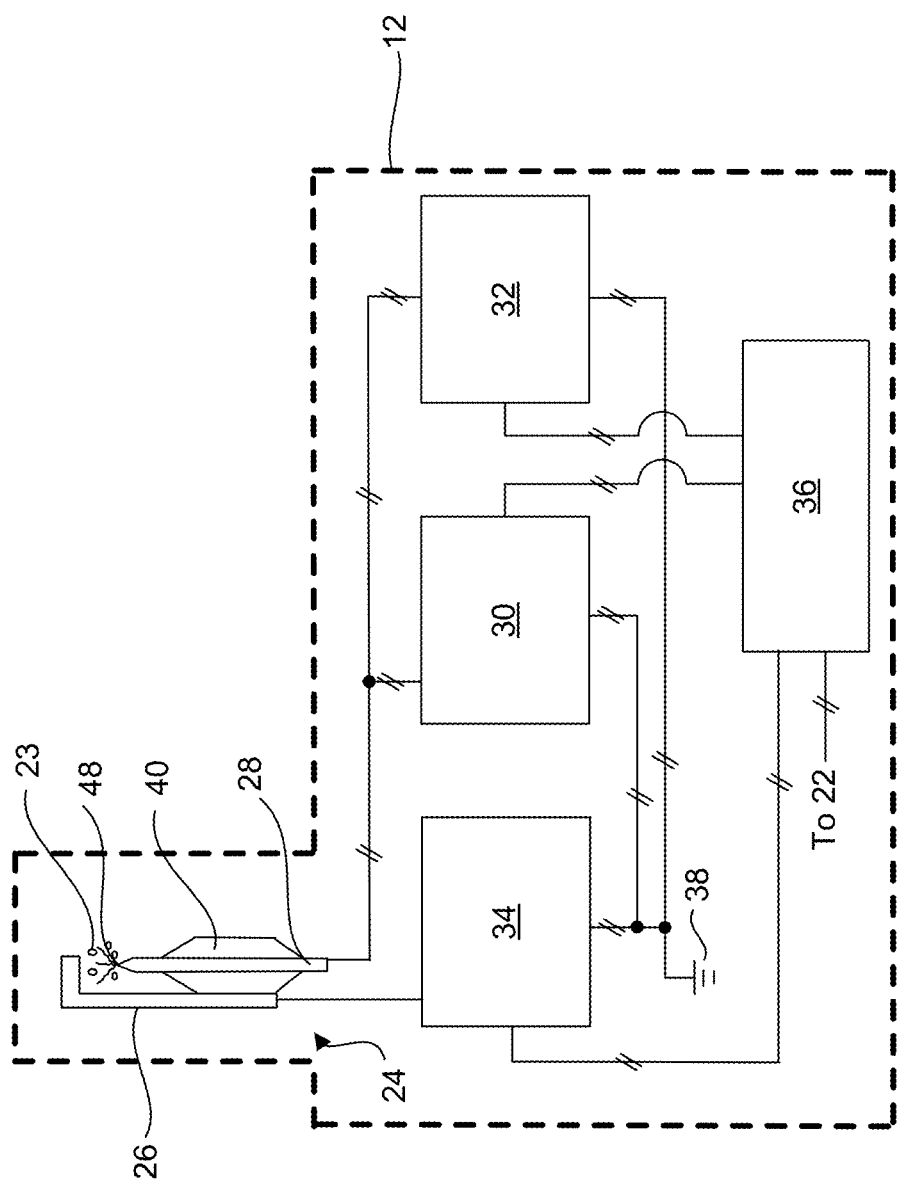
FIG. 2 is a diagrammatic illustration of an exemplary disclosed gas monitoring system that may be used in conjunction with the power system of FIG. 1.

As shown in FIG. 2, gas monitoring system 12 may include components that cooperate to identify particular constitute concentrations, for example concentrations of $NO_X$, $SO_X$, CO, $CO_2$, $NH_3$, within the exhaust gas 23 of power system 10 flowing through exhaust passage 18. Information regarding the gas constituents may then be utilized by system controller 22 to help regulate the different operations of power system 10. Gas monitoring system 12 may include, among other things, electrodes 24 (including at least one anode 26 and at least one cathode 28), a pulse generator 30, a voltage measurement device 32, a current measurement device 34, and a detection controller 36. Electrodes 24 may be positioned in fluid communication with the exhaust gas 23 of passage 18 such that a discharge path between anode 26 and cathode 28 may be created within the exhaust gas 23. Pulse generator 30, voltage measurement device 32, current measurement device 34, and detection controller 36 may be located anywhere onboard or in the immediate proximity to power system 10, and be in communication with each other, with electrodes 24, and/or with system controller 22.

Anode 26 may embody a conductive element, for example an element composed of carbon nanotubes, carbon fibers, stainless or non-stainless steel, tantalum, platinum, tungsten, silver, gold, high-nickel alloys, copper, or other conductive elements. During normal operation (e.g., when a negative voltage is applied to electrodes 24) anode 26 may be connected to an electrical ground 38, such as an earth ground, or other ground. In other operations (e.g., when a positive voltage is applied to electrodes 24), anode 26 may be insulated from ground 38 via an insulator 40.

Cathode 28 may also embody a conductive element substantially similar to anode 26. However, cathode 28, in contrast to anode 26 may be insulated from ground 38 via insulator 40 during normal operations, and connected to ground 38 during the other operations. Additionally, depending on the particular geometry of cathode 28 and/or anode 26, it may be necessary to insulate portions of cathode 28 from anode 26. Insulator 40 may include, for example, a material fabricated from aluminum oxide, aluminum nitride, porcelain, boron nitride, or other insulating elements.

Figure 3:
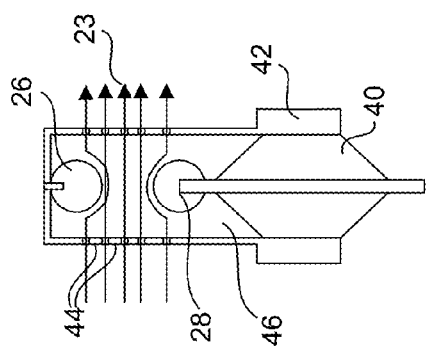
FIGS. 3-6 are schematic and diagrammatic illustrations of various electrode configurations that form a portion of the gas monitoring system of FIG. 2.
Figure 4:
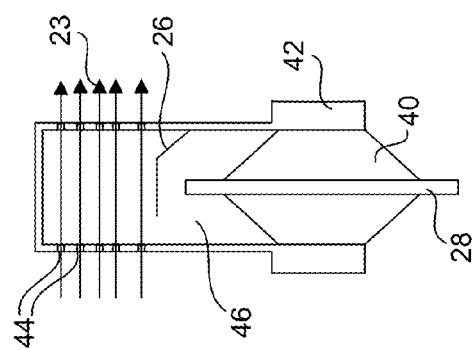
Figure 5:
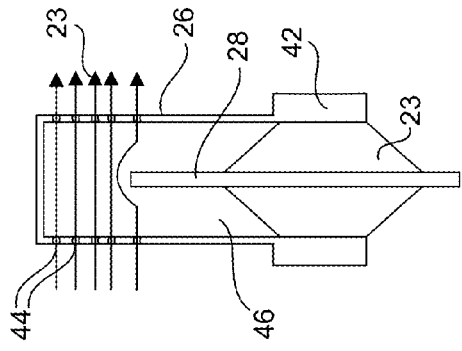
Figure 6:
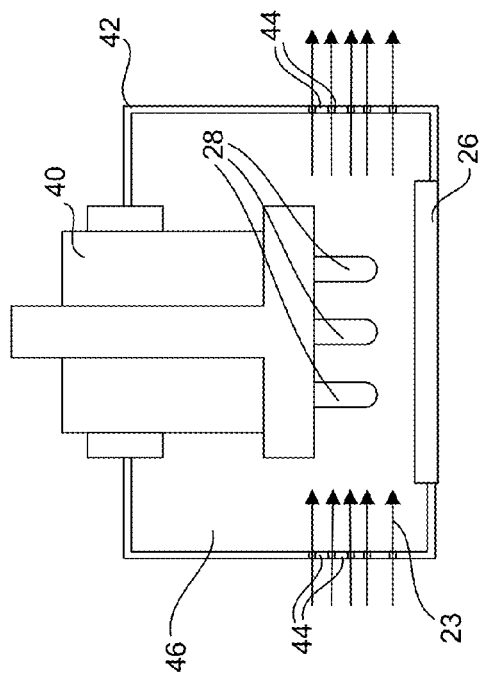

The configuration of electrodes 24 shown in FIG. 1 is known as a point-to-plane configuration. In this configuration, cathode 28 may come to a point and anode 26 may be generally planar and spaced apart from cathode 28 in an orthogonal orientation, such that a discharge of electricity may be possible from the point of cathode 28 to any location on anode 26. It should be noted, however, that many other electrode configurations are also possible. For example, FIG. 3 illustrates anode 26 and cathode 28 as generally spherical conductors. In this configuration, anode 26 may be electrically and mechanically coupled to an anode cap 42 that substantially surrounds cathode 28. Anode cap 42 may have a plurality of openings 44 that allow the exhaust gas 23 from power system 10 to pass through a discharge space 46 between anode 26 and cathode 28. In the configuration of FIG. 4, cathode 28 may be a generally cylindrical conductor, and anode 26 may be a conductor that is positioned generally perpendicular to cathode 28. FIG. 5 illustrates cathode 28 as being a generally cylindrical conductor located within anode cap 42, and anode 26 as being generally integral with anode cap 42 and coaxial to cathode 28. In this configuration, the discharge path between electrodes 24 may occur radially outward from cathode 28 to anode 26. Finally, FIG. 6 illustrates an electrode configuration having a multiple point-type cathode 28 that interacts with a single generally planar anode 26, which is generally perpendicular to cathode 28. The configuration of FIG. 6 may be capable of creating a multi-point discharge within the exhaust gas 23 between anode 26 and cathode 28. Additionally, in some embodiments (not shown), a dielectric may be located within the discharge path between cathode 28 and anode 26, for example as a coating on anode 26 and/or cathode 28.

Referring back to FIG. 2, the configuration of pulse generator 30 may be based on a capacitive architecture, an inductive architecture, or a combination thereof. A capacitive-based architecture may include one or more capacitors disposed in series (e.g., a capacitor bank) or in parallel (e.g., a Marx bank). An inductive-based architecture may include one or more magnetic inductors such as an induction coil also known as an inductive adder. A combination capacitive-inductive architecture may include both inductive and capacitive components coupled to function together through the use of magnetic compression. Additionally, in some embodiments, pulse generator 30 may use one or more transmission lines (e.g., a Blumlien), if desired. Pulse generator 30 may be a stand-alone component (shown in FIG. 2) or, alternatively, form an integral part of detection controller 36, as desired.

Pulse generator 30 may include or be connected to a source of electrical power (not shown). In one example, pulse generator 30 may include an integral energy storage device that functions as the source of electrical power. In another example, the energy storage device may be a separate unit, for example, a bank of one or more capacitors, a bank of one or more inductors, or a combination thereof. The energy storage device, in these embodiments, may be charged by a separate supply voltage (e.g., the voltage from an power system battery, a rectified utility voltage, etc.).

Pulse generator 30 may be controlled to generate and apply one or more positive or negative voltage pulses to electrodes 24 to cause a discharge between cathode 28 and anode 26 that creates a non-thermal plasma 48 in the exhaust gas 23 of power system 10 (to cause a partial discharge of one or more constituents in the exhaust gas 23). Pulse generator 30 may be configured to produce generally square shaped pulses or pulses that sweep through a range of voltage values (e.g. exponential voltage pulse, saw tooth voltage pulse, etc.). In some embodiments, pulse generator 30 may be capable of producing a continuous train (i.e., a series) of discrete pulses. Additionally, in some embodiments pulse generator 30 may vary the pulse amplitude from pulse to pulse in the train of pulses. It is contemplated that there may be additional pulse generators 30, such that each pulse generator 30 produces a different type or shape of pulse, as desired.

Each voltage pulse may be tuned to a specific constituent of the exhaust gas 23, such that a current observed during a partial discharge of the constituent is maximized for a given pressure and/or temperature. The tuned voltage pulse can be tied to an ionization cross-section of the particular constituent in the following manner. First, an electric field between the electrodes 24 may be calculated for each voltage pulse. The electric field may then be utilized to determine a kinetic energy of electrons within the gas constituent, from which an ionization cross-section of the constituent may be determined. The ionization cross-section may then be compared to a list of ionization cross-sections for known constituents, and the identity of the particular constituent under a given set of conditions may be determined.

Figure 7:
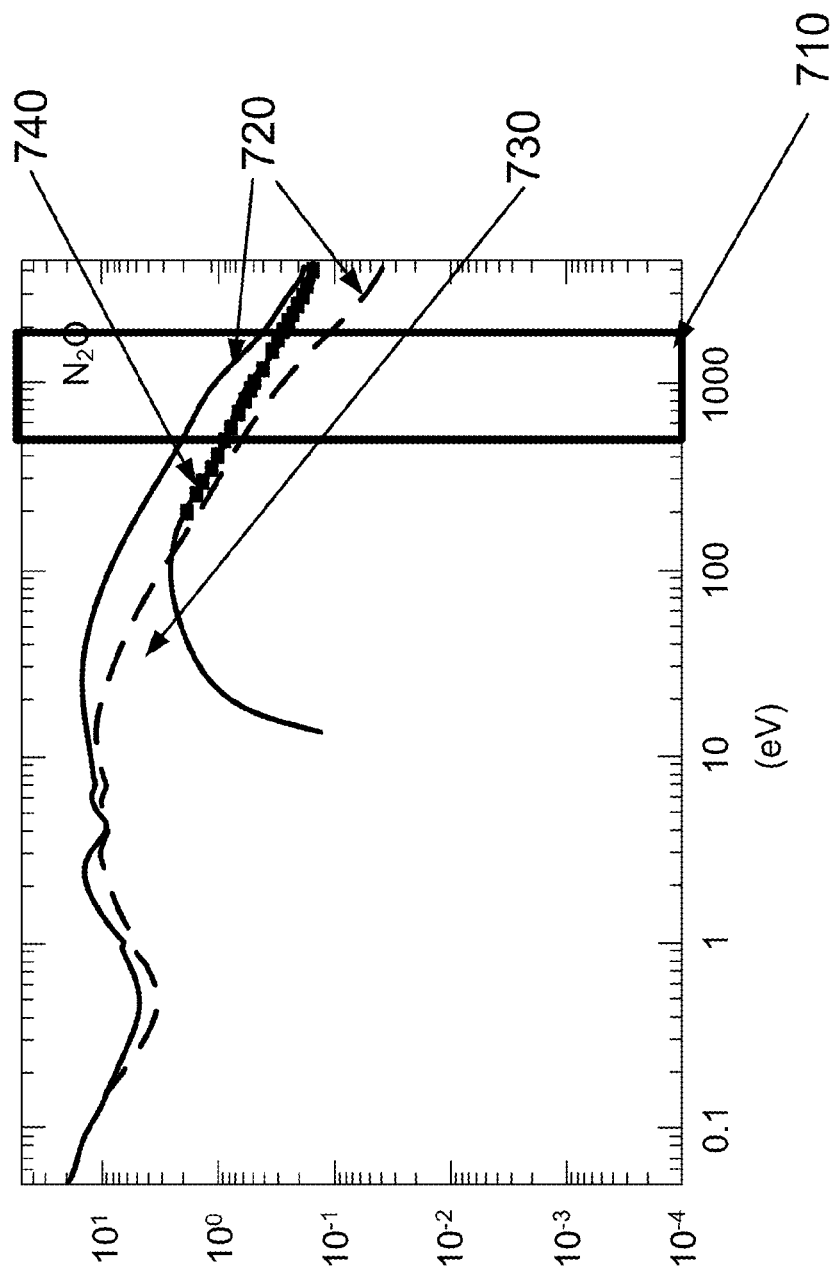
FIG. 7 is an exemplary graph showing ionization cross sections as a function of electron energy for $N_2O$.

Additionally, each voltage pulse may be controlled to form a non-thermal plasma and provide a low energy per pulse, creating conditions that may allow electron impact ionization to dominate the determination of ionization cross-section for the single gas constituent at a particular pressure and temperature. FIG. 7 illustrates a graph showing different mechanisms for ionization of a particular gas, for example $N_2O$, as functions of electron energy and ionization cross-section. The applied voltage pulses may be configured to produce a non-thermal plasma between electrodes 24, such that some electron energies created by the pulse are contained within the boxed region 710. In general, there are multiple pathways for determining ionization cross section over various electron energies (e.g., curves 720 and 730). However, many pathways may be neglected (e.g., curves 720 and 730) when a non-thermal plasma is used, which leaves electron impact ionization, curve 740, as the dominant process in determining ionization cross-section. Thus, a particular applied voltage pulse may be tuned to the ionization cross-section of a particular constituent, and the voltage pulse parameters and other information may be stored in a lookup table for later use in determining the identity and/or concentration of the particular constituent within the exhaust gas 23.

In general, the process of tuning the voltage pulse may involve applying a series of voltage pulses to test electrodes exposed to a substantially pure gas (i.e. single gas constituent) at a set pressure and a set temperature, wherein each subsequent voltage pulse in the series of voltage pulses has an incrementally higher voltage amplitude than a preceding voltage pulse. Each voltage pulse should be sufficient to create a non-thermal plasma between the test electrodes, and the energy of each applied pulse should be limited to about 5 mJ or less. The voltage amplitude of each subsequent pulse may be increased until a maximum current passes between the test electrodes. The voltage amplitude corresponding to maximum current may then be recorded into the lookup table for the particular constituent.

The output of pulse generator 30 may be current-limited, in some situations, to help ensure that a thermal plasma (e.g., an arc) does not form between electrodes 24 during discharge. In particular, one or more of a width, an amplitude, and a frequency of the pulse created by pulse generator 30 may be selectively adjusted by detection controller 36 to help ensure that the plasma 48 created between electrodes 24 is non-thermal. For example, the pulse width may be varied within a range of about 1-10 µs, while the pulse amplitude may be varied within a range of about 0.2 kV to 20 kV. Similarly, the pulse frequency may range from a single pulse to a pulse frequency in the kHz. In general, the pulse width, pulse amplitude, and pulse frequency should be set sufficiently high to ensure formation of plasma 48 between electrodes 24 during discharge, without causing the plasma 48 to become thermal. The energy dissipated per pulse should generally be about 5 mJ or less. However, if a sweeping voltage pulse is used, the energy per pulse may exceed 5 mJ due, in part, to the longer pulse needed to create partial discharges in multiple constituents. Prevention of a thermal plasma between electrodes 24 may help to reduce electrode erosion and energy supply requirements of gas monitoring system 12.

Voltage measurement device 32 may embody a voltage divider, for example a resistive or capacitive voltage divider, that is configured to measure an actual voltage across discharge space 46. Voltage measurement device 32 may be configured to generate a voltage signal indicative of the actual voltage and direct the voltage signal to detection controller 36 for further processing. It is contemplated that voltage measurement device 32 may additionally be configured to provide the voltage signal to another system or device, for example, to system controller 22 (referring to FIG. 1), to an oscilloscope, to an offboard computer, etc., if desired.

Current measurement device 34 may embody a current transformer configured to measure an actual current between electrodes 24 during discharge. Current measurement device 34 may be further configured to generate a current signal indicative of the actual current and direct the current signal to controller 36 for further processing. It is contemplated that current measurement device 34 may additionally be configured to provide the current signal to another system or device, for example, to system controller 22 (referring to FIG. 1), to an oscilloscope, to an offboard computer, etc., as desired.

Detection controller 36 may include a processor (not shown), a memory (not shown), and/or a data interface (not shown). The processor(s) may be a single or multiple microprocessors, field programmable gate arrays (FPGAs), or digital signal processors (DSPs) capable of executing particular sets of instructions. The instructions executed by the processor may be pre-loaded into the processor or may be stored in separate computer-readable memory (not shown) or other separate storage device (not shown), such as a random access memory (RAM), a read-only memory (ROM), a hard disk, an optical disk, a magnetic medium, a flash memory, other permanent memory, other volatile memory, or any other tangible mechanism capable of providing instructions to the processor. Additionally, one or more lookup tables (not shown) may be stored in the processor and/or separate computer-readable memory, as desired, and referenced by the processor during execution of the instructions.

It should be appreciated that detection controller 36 could be dedicated to only gas monitoring functions or, alternatively, integral with general system controller 22 (referring to FIG. 1) and be capable of controlling numerous power system functions and modes of operation. If separate from system controller 22, detection controller 36 may communicate with system controller 22 via data links or other methods. Various other known circuits may be associated with detection controller 36, including power supply circuitry, signal-conditioning circuitry, actuator driver circuitry (i.e., circuitry powering solenoids, motors, or piezo actuators), communication circuitry, and other appropriate circuitry. In some embodiments, detection controller 36 may be coupled to input/output devices (e.g., to a monitor, a keyboard, a printer, etc.) to receive input from a user and output information to the user. Detection controller 36 may be configured to communicate with other systems and/or devices, for example, an oscilloscope, a computer, etc., as desired. Additionally, in some embodiments, detection controller 36 may be configured to send control signals or otherwise communicate with one or all of pulse generator 30, voltage measurement device 32, current measurement device 34, and electrodes 24.

The lookup table used by the controller 36 may contain information used to determine the identities and concentrations of different constituents within the exhaust gas 23 of power system 10. For example, the lookup table may include voltage values tuned to correlate with partial discharge events of particular constituents in the exhaust gas 23 of power system 10, at a particular pressure and a particular temperature. Under normal conditions (i.e., when a voltage pulse is not applied to electrodes 24), the exhaust gas between anode 26 and cathode 28 may function as an insulator, preventing electricity from being conducted therebetween. However, a period of time after a known pulse of electrical energy having a sufficiently high voltage is first applied to electrodes 24 (i.e., a period of time after a voltage exceeding a dielectric strength of constituents in the exhaust gas 23 is first applied to electrodes 24), constituents in the exhaust gas 23 between electrodes 24 may begin to "break down" or partially ionize and function as a conductor to conduct the energy from cathode 28 to anode 26. When the applied voltage pulse is tuned to a particular constituent at low energies, for example, at about 5 mJ or less, a partial discharge should occur, during which the current should spike to an expected level that correlates to the concentration of the particular constituent. Similarly, if a swept voltage pulse is greater than the tuned voltage value of a particular constituent, and the pulse energy is below the breakdown voltage, a partial discharge may occur, during which a spike in current may occur that correlates to the concentration of the constituent. Moreover, the above process may be used to determine concentration information regarding a concentration of a particular constituent within a gas containing a plurality of constituents. In this case, however, the partial discharge occurs in a gas containing a plurality of constituents, where the concentration of each gas is known. The look up table may include the tuned parameters for the voltage pulse associated with each constituent of interest, with respect to changes in operating configurations and conditions (e.g., gas pressure, gas temperature, gas mixture, and electrode configuration). The lookup table may store these different tuned voltage parameters, along with the corresponding conditions under which partial discharge should occur.

In addition, the concentration (K) of each possible constituent in the exhaust gas 23 may be pre-calculated as a function of a measured current, and stored in the lookup table. Measured current values (i.e., values associated with the current signal generated by current measurement device 34) that occur during breakdown events may then be referenced by detection controller 36 with values stored in the lookup table to determine concentrations of particular constituents of the exhaust gas 23. The function used to pre-calculate the concentrations of particular constituents may be represented by Eq. 1 below:

$$K = A \cdot J; \qquad \text{Eq. 1}$$

wherein:
  A is a constant; and
  J is the measured current

The A values for Eq. 1 may be determined via the Loshmidt Number and a real volume of the discharge, using a gas analyzer for calibration. Once A has been determined over a range of values for a particular gas constituent, in a gas containing multiple constituents, under different conditions (e.g., varying pulse parameters, pressure, temperature, electrode configurations, and concentration), these values may be stored in the lookup table for use by detection controller 36.

One or more parameter sensors may be associated with detection controller 36 to facilitate determination of the constituent concentration within the exhaust gas 23 of power system 10. For example, a temperature sensor 50 and/or a pressure sensor 52 may be disposed in fluid communication with the exhaust gas 23 of passage 18 at locations near electrodes 24, and be configured to generate corresponding signals directed to detection controller 36. Detection controller 36 may be configured to determine the conditions (e.g., temperatures and/or pressures of the exhaust gas 23) during a constituent breakdown event based on the signals, and affect use of the lookup tables accordingly. It is contemplated that the conditions may alternatively be calculated from other measured parameters, instead of being directly measured, if desired. It is also contemplated that sensors other than a temperature sensor or a pressure sensor may be utilized, if desired, to sense other parameters of exhaust gas 23 for use in determining the constituent identity and/or concentration.

Detection controller 36 may regulate operation of pulse generator 30 to selectively cause a partial discharge of different constituents assumed to be contained within the exhaust gas of power system 10. In particular, detection controller 36 may be configured to dynamically adjust a voltage, a width, and/or a frequency of the pulse generated by pulse generator 30 to conform to a voltage pulse tuned to a particular gas constituent (as contained within the lookup table), at a particular pressure and temperature. Detection controller 36 may be configured to reference signals from voltage measurement device 32 and current measurement device 34 at the time the partial discharge of the expected constituent occurs, with the lookup table to identify the concentration of the expected constituent. In some situations, detection controller 36 may benefit from noise reduction and/or filtering on the voltage and current signals during the analysis. Alternatively, detection controller 36 may be configured to simply trigger pulse generator 30 to generate one or more swept voltage pulses (e.g., saw tooth, exponential, etc.), whose pulse amplitude is greater than or equal to the largest tuned voltage of the expected constituents in the gas. Additionally, in some embodiments, detection controller 36 may be configured to trigger pulse generator 30 to generate one or more swept voltage pulses, whose amplitude ranges from a value below the lowest tuned voltage of the expected constituents in the gas to an amplitude greater than or equal to the largest tuned voltage of the expected constituents in the gas, or vice versa. Additionally, detection controller 36 may be configured to trend changes in gas composition over time and/or under different operating conditions of power system 10, as desired.

It is contemplated that detection controller 36 may take specific corrective actions in response to detection of particular constituents and/or their concentrations. The corrective actions may include, for example, coordinating with system controller 22 to make adjustments to the operation of power system 10, activation of alarms or alerts when a threshold level of a particular gas constituent is reached, regulation of gas mixing, and other actions known in the art.

In another embodiment, detection controller 36 may be configured to use electrodes 24 to determine parameters of exhaust gas 23, for example, gas pressure or gas temperature. In particular, detection controller 36 may be configured to apply a voltage pulse to electrodes 24 to cause breakdown of the exhaust gas 23, in a manner similar to what was described above. Detection controller 36 may then reference signals from voltage measurement device 32 and/or current measurement device 34 at the time of constituent breakdown, along with an elapsed period of time since application of the voltage pulse, with the lookup tables to determine the parameters of the exhaust gas 23. It is contemplated that detection controller 36 may be configured to alternatively calculate the parameters based on the signal from voltage measurement device 32, the signal from current measurement device 34, and the elapsed period of time, without the use of the lookup table, if desired. In some situations, detection controller 36 may benefit from noise reduction and/or filtering on the voltage and current signals during the analysis.

FIGS. 8-12 illustrate exemplary operations performed by detection controller 36. FIGS. 8-12 will be discussed in more detail in the following section to further illustrate the disclosed concepts.

INDUSTRIAL APPLICABILITY

The gas monitoring system of the present disclosure may be used in any application where it is desirable to identify concentrations of expected constituents in a gas. The gas monitoring system may identify concentrations of a constituent in a gas by selectively creating a non-thermal plasma in the gas using a voltage pulse tuned to a particular constituent of interest, and measuring a resulting current associated with the plasma. Alternatively, the disclosed gas monitoring system may identify concentrations of all expected constituents of a gas by using a swept voltage pulse whose maximum amplitude is greater than all of the tuned voltage values of the constituents of interest, and relating a current associated with the partial discharge of each of the constituents of interest to their concentrations. Potential applications for the disclosed gas monitoring system include, among others, hazardous or toxic gas handling applications; gas mixing applications; and engine system applications. Operation of gas monitoring system 12 will now be described in detail.

Figure 8:
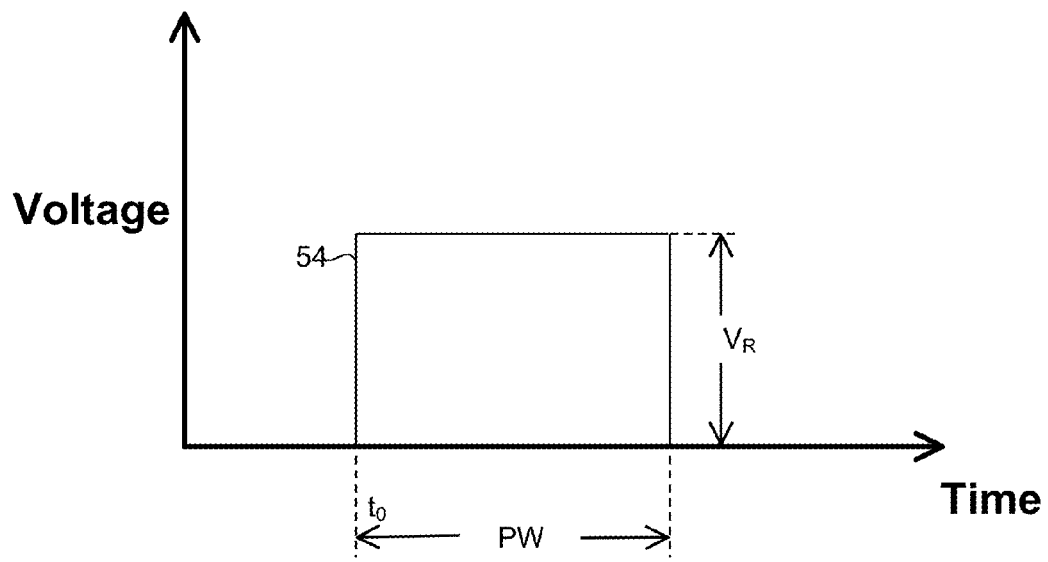
FIG. 8 is an exemplary voltage pulse associated with operation of the gas monitoring system of FIG. 2.
Figure 9:
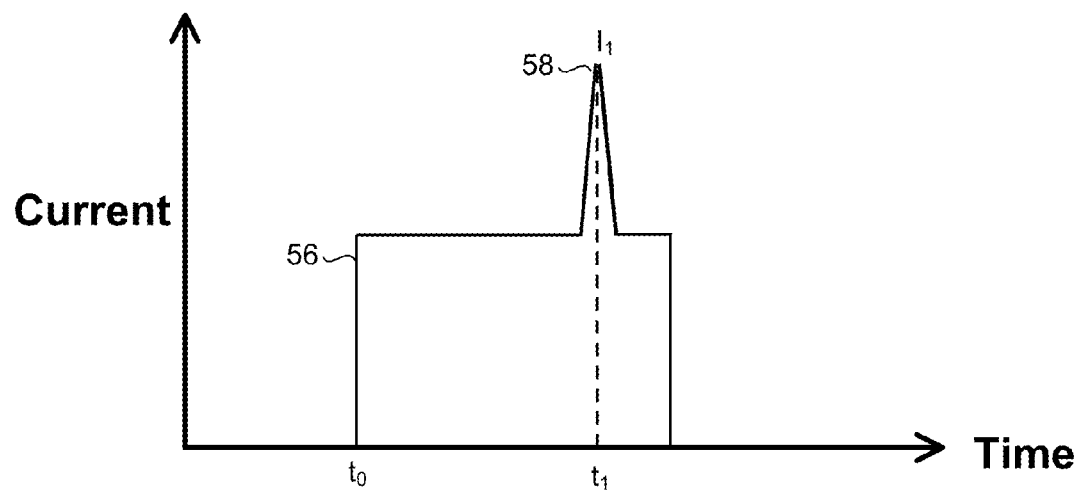
FIG. 9 is an exemplary current pulse associated with the voltage pulse of FIG. 8.

During operation of gas monitoring system 12, detection controller 36 may cause pulse generator 30 to generate and apply a voltage pulse to electrodes 24, thereby creating a non-thermal plasma 48 between electrodes 24. The voltage pulse may have an amplitude of $V_A$, a pulse width of PW, a pulse frequency of F, and an energy of about 5 mJ or less. The pulse energy should be such that a partial discharge occurs. In some situations, detection controller 36 may control the parameters of a single voltage pulse generated by pulse generator 30 to induce a partial discharge of all gas constituents of interest. In other situations, however, the parameters of the voltage pulse may be controlled (i.e. according to tuned parameters contained within the lookup table) to initiate a partial discharge of fewer than all of the gas constituents, for example only one particular gas constituent. FIG. 8, shows an exemplary voltage pulse 54, having a voltage pulse amplitude $V_R$ tuned to the constituent X within the exhaust gas 23. During application of the voltage pulse 54 a quasi-resonance in the current of the partial discharge of the constituent may occur, manifesting as a spike in the current. As shown in FIG. 9, the current pulse 56 across electrodes 24 resulting from the voltage pulse of FIG. 8, includes a current spike 58 at a time $t_1$ having an amplitude of $I_1$. This current spike 58 may correspond with a partial discharge of a constituent X expected to be included in the exhaust gas 23.

For the purposes of this disclosure, a spike in current may refer to a characteristic of a measured current, where the measured current rapidly increases for a brief period of time beyond an amplitude normally expected during and after an applied voltage pulse, and then rapidly decrease back to the expected amplitude. The spike may occur for only a very short amount of time, e.g., less than a micro second.

During and after the application of the voltage pulse 54, the voltage and current between electrodes 24 may be monitored by detection controller 36 via voltage measurement device 32 and current measurement device 34, respectively. Detection controller 36 may also track elapsed periods of time since initiation of the current pulse 56 and occurrence of different spikes in measured current. In addition, detection controller 36 may be programmed with or otherwise be able to detect the existing configuration of electrodes 24 (e.g., the type of, composition, and/or spacing between anode 26 and cathode 28), and monitor current operating parameters (e.g., pressure, temperature, etc.) of exhaust gas 23 in the presence of electrodes 24 via sensors 50, 52.

Detection controller 36 may be configured to determine the concentrations of gas constituent X based on the current measured between electrodes 24. For example, the concentration of constituent X may be determined by comparing a first current spike, alone or along with a time duration from $t_0$ to a time corresponding with observance of the current spike, with data in the lookup table.

A second constituent Y may be determined in the gas by applying a second voltage pulse (not shown) tuned to constituent Y. Following the same process described above the concentration of Y may then be determined. This process may repeat until all of the concentrations of the expected gas constituents are determined. In some cases, additional parameters (e.g., temperature, pressure, and/or electrode configuration) may be used in combination with time duration and/or current values to calculate gas constituent concentration.

Figure 10:
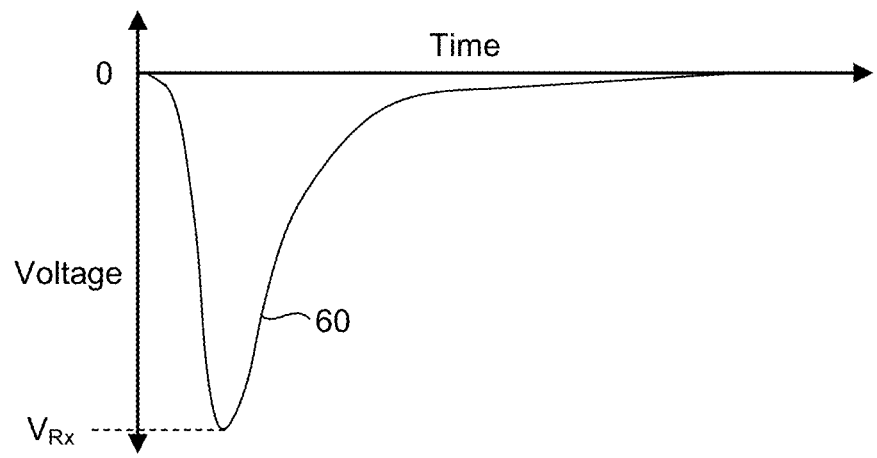
FIG. 10 is an exemplary exponential voltage pulse associated with operation of the gas monitoring system of FIG. 2.
Figure 11:
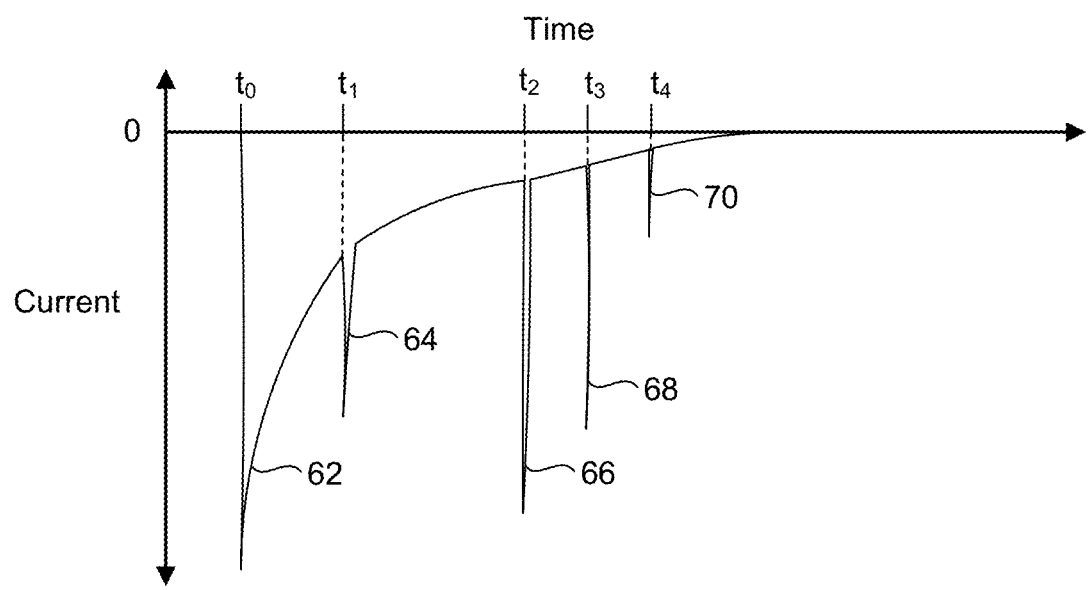
FIG. 11 is an exemplary current pulse associated with the voltage pulse of FIG. 10.

Alternatively, a single swept voltage pulse may be used to identify the concentrations of all the expected constituents. An example of a swept voltage pulse, may be an exponential voltage pulse. FIG. 10, shows an exemplary negative exponential voltage pulse 60 that can be applied to a gas containing at least the constituents $O_2$, NO, $NO_2$, and $N_2$. The amplitude of the applied exponential pulse may cover a range of values, with a minimum exponential voltage amplitude being less than the tuning voltage amplitudes of constituents $O_2$, NO, $NO_2$, and $N_2$, and the maximum amplitude of the exponential pulse voltage may be greater than or equal to the tuning voltage amplitudes of constituents $O_2$, NO, $NO_2$, and $N_2$. The corresponding current pulse 62, may have additional current spikes 64, 66, 68, and 70, that occur at times $t_1$, $t_2$, $t_3$, and $t_4$, respectively.

Detection controller 36 may be programmed with the identities of the constituents expected to be in the exhaust gas 23, as well as the order in which partial discharges of the constituents are expected to occur. That is, the constituent with the largest ionization cross-section should correspond to the spike at $t_1$, the constituent with the next largest ionization cross-section should correspond to the spike at $t_2$, and so on, until the spike occurs corresponding to the constituent with the lowest ionization cross-section. In this example, spikes 64, 66, 68, and 70, may correspond to $O_2$, $NO$, $NO_2$, and $N_2$, respectively. Detection controller 36 may be configured to match the amplitude of each current spike with constituent data stored in the lookup table to determine the concentration of each constituent.

In some embodiments, detection controller 36 may be able to monitor the current over only a specific time period in which the spike is expected to occur. For example, detection controller 36 may reference the lookup table for an expected time $t_1$ at which a spike for $O_2$ is expected to occur, and then monitor the current signal only during a range of times centered around $t_1$.

In some situations, the lookup table may not have data corresponding to the measured voltage values, the time durations, the measured current values, the electrode configuration, and/or the parameter of the exhaust gas 23. In these situations, any measured current spike(s) may be determined to be caused by electrical noise or an unexpected constituent within the fluid. When this occurs, detection controller 36 may notify a user of gas monitoring system 12 of the anomalous result.

In some embodiments, the measured voltage and current may be stored in a buffer between the applications of subsequent voltage pulses, which may occur, for example, at a repetition frequency between about 50 kHz to 60 kHz. The measured voltage and current may be stored until some threshold is met within the buffer (e.g., data from 1000 pulses may be stored in the buffer). Once the threshold is met, detection controller 36 may perform error reduction on the measured data in the buffer, before determining the identities and/or concentrations of the constituents. For example, detection controller 36 may average the buffer values for the voltage pulses, the current pulses, the current spikes, and/or the time durations. Detection controller 36 may then use the averaged values to identify the concentrations of the gas constituents. Detection controller 36 may maintain a first-in-first-out queue, such that the average buffer data is continually being updated. Alternatively, detection controller 36 could process the buffer values in blocks. For example, detection controller may average the first 1000 values and then wait until the buffer fills again to process the next 1000 values, etc.

Several advantages may be associated with gas monitoring system 12. For example, gas monitoring system 12 may be capable of rapidly identifying concentrations of different constituents of a gas using a single, short, voltage pulse, which may help to reduce energy consumption. Moreover, the plasma created between electrodes 24 may be a non-thermal plasma, which may help to reduce potential electrode erosion. Additionally, the higher temperature normally associated with thermal discharges for gas detection applications may be unnecessary, and the energy required to create the thermal plasma may be conserved.

Gas monitoring system 12 may also or alternatively be utilized to determine a parameter of exhaust gas 23, with or without determining the identities or concentrations of the exhaust gases. For example, detection controller 36, of the embodiment shown in FIG. 1, may cause pulse generator 30 to generate and apply a series of voltage pulses to electrodes 24, each subsequent pulse in the series having an incrementally greater pulse amplitude, until breakdown of the exhaust gas 23 is observed at a pulse amplitude, $V_A$. The voltage may increment via a linear increase. Alternatively, the voltage increment may occur in substantially equal steps of increasing voltage, if desired. In some embodiments, the steps of increasing voltage may be increased by non-equal amounts (e.g., initial step may be large, followed by progressively smaller steps), if desired. Detection controller 36 may then reference the $V_A$ that caused the breakdown, along with a known pressure value for the exhaust gas 23, with the lookup table to determine the corresponding temperature of the exhaust gas 23. Pressure of the exhaust gas 23 may be determined in a similar manner, through the use of a known temperature value for the exhaust gas 23.

Alternatively, detection controller 36 may be configured to calculate the temperature and/or pressure of the exhaust gas without the use of the lookup table, according to Paschen's Law below:

$$V_A = 0.386 \cdot \frac{P \cdot d}{k} \cdot \frac{P}{T} \cdot \frac{B}{\ln\left[\frac{P \cdot d}{A}\right]}$$

wherein:
  $V_A$ is the breakdown voltage;
  P is the known pressure of the exhaust gas 23;
  d is a known distance between anode 26 and cathode 28;
  T is the temperature being determined;
  k is the Boltzmann constant; and
  A and B are constants associated with the exhaust gas 23.
or wherein:
  $V_A$ is the breakdown voltage;
  P is the pressure being determined;
  d is a known distance between anode 26 and cathode 28;
  T is the known temperature of the exhaust gas 23;
  k is the Boltzmann constant; and
  A and B are constants associated with the exhaust gas 23.

In some situations, it may be necessary to determine the temperature of the exhaust gas 23, without having prior knowledge of the exhaust gas pressure (pressure could then be determined using Paschen's Law based on this independently determined temperature according to the method outlined above). During operation of the gas monitoring system 12 depicted in FIGS. 1 and 2, when detection controller 36 causes pulse generator 30 to generate and apply the voltage pulses to electrodes 24, thereby creating the non-thermal plasma 48 (or in alternative embodiments a thermal plasma) between electrodes 24 and causing the exhaust gas 23 breakdown, detection controller 36 may analyze the current measured at electrodes 24 via current measurement device 34.

Figure 12:
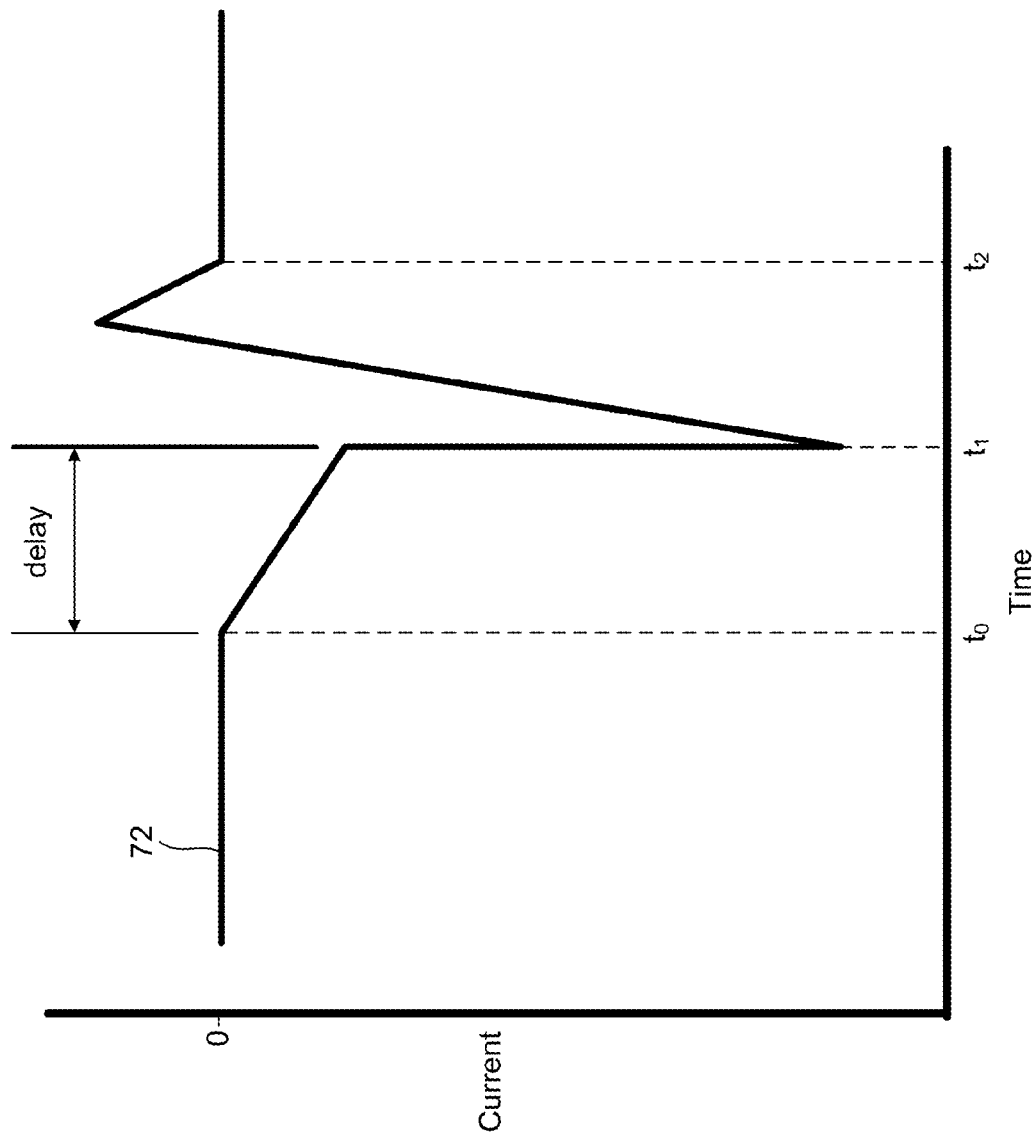
FIG. 12 is a graph depicting an exemplary operation of the gas monitoring system of FIG. 2.

As can be seen in a current trace 72 of FIG. 12, the current measured at electrodes 24 may start to deviate away from about zero at a time $t_0$ corresponding to breakdown of the exhaust gas 23. At time $t_0$ the exhaust gas 23 starts to ionize due to application of the voltage pulse and the exhaust gas 23 may start to pass current between electrodes 24. As breakdown of the exhaust gas continues, the amount of current passed between electrodes 24 may slowly increase to a threshold point, at which plasma 48 is created with discharge gap 46, allowing a maximum amount of current to flow between electrodes 24. This time may correspond with the spike in current shown at time $t_1$ in trace 72 of FIG. 12. After the end of the voltage pulse, the current passing between electrodes 24 may quickly drop back to about zero at a time $t_2$.

The time period between $t_0$ and $t_1$ (i.e., the time between when current begins to flow between electrodes 24 and when the current flow spikes to a maximum) may be known as a current delay.

During the current analysis performed at the time of breakdown, detection controller 36 may identify the current delay described above, and relate the delay to the temperature of the exhaust gas 23. In particular, detection controller 36 may determine the temperature of the exhaust gas 23 by measuring the delay and referencing the delay with the lookup table.

It will be apparent to those skilled in the art that various modifications and variations can be made to the system of the present disclosure without departing from the scope of the disclosure. Other embodiments will be apparent to those skilled in the art from consideration of the specification and practice of the system disclosed herein. For example, although described throughout as using a non-thermal plasma to determine concentrations of constituent, it is contemplated that the output of pulse generator 30 may result in a thermal discharge, if desired. Additionally, the energy per pulse in the disclosed embodiments may exceed 5 mJ per pulse, in some situations. It is intended that the specification and examples be considered as exemplary only, with a true scope of the disclosure being indicated by the following claims and their equivalents.

What is claimed is:

1. A gas monitoring system, comprising:
a first electrode;
a second electrode spaced apart from the first electrode to receive a gas between the first and second electrodes;
a pulse generator configured to apply a voltage pulse to the first and second electrodes and create a non-thermal plasma between the first and second electrodes; and
a detection controller in communication with the pulse generator and configured to:
acquire an actual current between the first and second electrodes during application of the voltage pulse;
determine a concentration of a constituent of the gas based on the actual current and an expected identity of the constituent;
detect a spike in the actual current during or after the application of the current pulse; and
correlate the spike to the concentration of the expected constituent.

2. The gas monitoring system of claim 1, wherein the voltage pulse is tuned to a value that corresponds to the expected identity of the constituent.

3. The gas monitoring system of claim 1, further including a voltage measuring device configured to measure the actual voltage between the first and second electrodes and generate a signal indicative of the actual voltage that is directed to the detection controller.

4. The gas monitoring system of claim 1, further including a current measuring device configured to measure the actual current between the first and second electrodes, wherein the current measuring device is configured to generate a signal indicative of the actual current that is directed to the detection controller.

5. The gas monitoring system of claim 1, wherein the detection controller includes a table stored in memory that relates a value of the spike to the concentration of the constituent.

6. The gas monitoring system of claim 5, wherein the table stored in memory relates a tuned voltage value to one or more expected constituents.

7. The gas monitoring system of claim 6, wherein:
the constituent is a first constituent;
the spike is a first spike in the actual current associated with a partial discharge of the first constituent;
the pulse generator is further configured to apply a second voltage pulse, tuned to a second constituent of the gas, to the first and second electrodes and create a non-thermal plasma between the first and second electrodes; and
the detection controller is further configured to:
detect a second spike in the actual current during application of the second voltage pulse; and
determine a concentration of the second constituent of the gas based on the actual current and an expected identity of the second constituent.

8. The gas monitoring system of claim 7, wherein:
the gas is exhaust gas from an engine; and
the first and second constituents are selected from the group consisting of $NO_X$, $NH_3$, $CO$, $CO_2$, and $SO_X$.

9. The gas monitoring system of claim 1, wherein the detection controller is further configured to: average values of the spike for multiple current pulses; and
identify" the constituent concentrations based on the average values.

10. The gas monitoring system of claim 1, wherein the voltage pulse is an exponential voltage pulse.

11. The gas monitoring system of claim 10, wherein:
the constituent is a first constituent;
the spike is a first spike in current associated with a partial discharge of the first constituent; and
the detection controller is further configured to:
detect a second spike in the actual current during or after application of the voltage pulse; and
determine a concentration of a second constituent based on the second spike and an expected identity of the second constituent.

12. The gas monitoring system of claim 1, wherein the detection controller is further configured to:
compare the concentration of the constituent to a threshold; and
implement corrective action when the concentration is greater than the threshold.

13. The gas monitoring system of claim 12, wherein the corrective action includes coordinating with a power system controller to adjust operation of a power system.

14. The gas monitoring system of claim 13, wherein the corrective action includes activating an alarm.

15. The gas monitoring system of claim 1, wherein:
the first electrode is a cathode;
the second electrode is an anode; and
the voltage pulse is negative, such that current flows from the cathode to the anode during application of the voltage pulse.

16. The gas monitoring system of claim 1, wherein the detection controller is further configured to determine the constituent concentration based on a known configuration of the first and second electrodes.

17. The gas monitoring system of claim 16, wherein the known configuration includes a point-to-plane configuration.

18. The gas monitoring system of claim 16, wherein the known configuration includes the first and second electrodes being generally spherical.

19. The gas monitoring system of claim 16, wherein the known configuration includes the first electrode being a cathode, the second electrode being an anode, and an anode cap connected to the anode and substantially enclosing the cathode.

20. The gas monitoring system of claim 16, wherein the known configuration includes the first and second electrodes being coaxial.

21. The gas monitoring system of claim 16, wherein the known configuration includes the first electrode being a multi-point cathode, and the second electrode being a generally planar anode.

22. A gas monitoring system, comprising:
a first electrode;
a second electrode spaced apart from the first electrode to receive a gas between the first and second electrodes;
a pulse generator configured to apply a series of voltage pulses to electrodes exposed to the gas, wherein each voltage pulse in the series of voltage pulses has an incrementally higher voltage amplitude than a preceding voltage pulse in the series of voltage pulses; and
the detection controller is configured to:
   acquire an actual current between the first and second electrodes during application of each of the series of voltage pulses;
   acquire a first parameter of the gas; and
   determine a second parameter of the gas based on a known first parameter of the gas and a voltage amplitude of the one of the series of voltage pulses,
   wherein the first parameter is one of temperature and pressure of the gas and the second parameter is the other of temperature and pressure of the gas.

23. The gas monitoring system of claim 22, wherein the pulse generator is configured control the applied voltage pulses to generate a non-thermal plasma within the gas.

24. A gas monitoring system, comprising:
a first electrode;
a second electrode spaced apart from the first electrode to receive a gas between the first and second electrodes;
a pulse generator configured to apply a voltage pulse to the first and second electrodes and create a plasma between the first and second electrodes; and
a detection controller is configured to:
acquire an actual current between the first and second electrodes during application of the voltage pulse;
determine a delay associated with the current between the electrodes at a start of breakdown of the gas caused by application of the voltage pulse; and
determine a temperature of the gas based on the delay.

25. The gas monitoring system of claim 24, wherein the detection controller is configured to determine a pressure of the gas based on temperature of the gas.

26. A power system, comprising:
an engine configured to generate a flow of exhaust gas;
a passage connected to the engine and configured to direct the exhaust gas from the engine to the atmosphere;
a system controller configured to regulate operation of the engine;
an anode disposed in fluid communication with the passage;
a cathode disposed in fluid communication with the passage and spaced apart from the anode to receive at least a portion of the exhaust gas between the anode and the cathode;
a pulse generator configured to apply a voltage pulse to the anode and the cathode to create a non-thermal plasma in the exhaust gas;
a voltage measuring device configured to measure an actual voltage between the anode and the cathode;
a current measuring device configured to measure an actual current between the anode and the cathode and generate a signal indicative of the actual current; and
a detection controller in communication with the system controller, the pulse generator, the voltage measuring device, and the current measuring device, and being configured to:
   determine a concentration of a constituent based on the current signal and the expected identity of the constituent; and
coordinate with the system controller to adjust operation of the engine based on the concentration of the constituent.

27. A gas monitoring system, comprising:
a first electrode;
a second electrode spaced apart from the first electrode to receive a gas between the first and second electrodes;
a pulse generator configured to apply a voltage pulse to the first and second electrodes and create a non-thermal plasma between the first and second electrodes; and
a detection controller in communication with the pulse generator and configured to:
acquire an actual current between the first and second electrodes during application of the voltage pulse;
and determine a concentration of a constituent of the gas based on the actual current and an expected identity of the constituent, wherein the voltage pulse is tuned to a value that corresponds to the expected identity of the constituent.

* * * * *